US008222199B2

(12) United States Patent
Fehr et al.

(10) Patent No.: US 8,222,199 B2
(45) Date of Patent: Jul. 17, 2012

(54) PERFUMING INGREDIENTS WITH SAFFRON ODOR

(75) Inventors: Charles Fehr, Versoix (CH); Pierre-Alain Blanc, Geneva (CH)

(73) Assignee: Firmenich SA, Geneva (CH)

(*) Notice: Subject to any disclaimer, the term of this patent is extended or adjusted under 35 U.S.C. 154(b) by 638 days.

(21) Appl. No.: 11/677,979

(22) Filed: Feb. 22, 2007

(65) Prior Publication Data

US 2007/0149438 A1 Jun. 28, 2007

Related U.S. Application Data

(63) Continuation of application No. PCT/IB2005/002645, filed on Sep. 7, 2005.

(30) Foreign Application Priority Data

Sep. 14, 2004 (WO) .................. PCT/IB2004/003032

(51) Int. Cl.
*A61K 8/37* (2006.01)

(52) U.S. Cl. ................ 512/22; 512/23; 512/24; 512/25; 512/26

(58) Field of Classification Search .............. 512/22–25, 512/26
See application file for complete search history.

(56) References Cited

U.S. PATENT DOCUMENTS

| | | | | |
|---|---|---|---|---|
| 4,411,829 | A | 10/1983 | Schulte-Elte et al. | 252/522 |
| 6,177,400 | B1 * | 1/2001 | Mimoun et al. | 512/24 |
| 2003/0119712 | A1 * | 6/2003 | Fehr et al. | 512/1 |

FOREIGN PATENT DOCUMENTS

| | | | |
|---|---|---|---|
| CH | 680 853 | A5 | 11/1992 |
| EP | 0 955 290 | A1 | 11/1999 |
| EP | 1 318 144 | A1 | 6/2003 |

OTHER PUBLICATIONS

CAS reg. No. 179104-41-7, Aug. 6, 1996.*
CAS reg. No. 100520-15-8, Mar. 1, 1986.*
Kin-Fai Cheng et al., "Synthesis of inverto-yuehchukene and its 10-(indol-3'-yl) isomer. X-Ray structure of (4aRS,IOaRS)-1,1,3-trimethyl-1,2,4a,5,10,10a hexahydroindene [1,2-b]indol-10-one", Journal of Chem. soc., Perkin Trans. 1, pp. 1213-1217 (1996).
William F. Erman et al., "Base Cleavage of β,γ-Unsaturated Bicyclic Cyclobutanones", The Journal of Organic Chemistry, vol. 34, No. 7, pp. 2196-2203 (1969).
I. Alkonyi et al., "Synthesis of a Trimethyl Cyclohexadiene Carboxylic Acid"pp. 294-293 (1957).
I. Alkonyi et al., "Synthesis of a Trimethyl Cyclohexadiene Carboxylic Acid", Acta Chimica Academiae Scientiarium Hungaricae 1957, vol. 12, pp. 289-294 (1957).

* cited by examiner

*Primary Examiner* — Douglas Mc Ginty
(74) *Attorney, Agent, or Firm* — Winston & Strawn LLP

(57) ABSTRACT

The present invention concerns the use as perfuming ingredient of a lower alkyl ester of 4,6,6-trimethyl-1,3-cyclohexadiene-1-carboxylate or 4,6,6-trimethyl-3-cyclohexene-1-carboxylate. These compounds are able to impart odor notes of the spicy/saffron type.

7 Claims, No Drawings

PERFUMING INGREDIENTS WITH SAFFRON ODOR

CROSS-REFERENCE TO RELATED APPLICATIONS

This application is a continuation of International application PCT/IB2005/002645 filed Sep. 7, 2005, the entire content of which is expressly incorporated herein by reference thereto.

TECHNICAL FIELD

The present invention relates to the field of perfumery and particularly to the use as perfuming ingredient of a lower alkyl ester of 4,6,6-trimethyl-1,3-cyclohexadiene-1-carboxylate or 4,6,6-trimethyl-3-cyclohexene-1-carboxylate.

BACKGROUND

The methyl and ethyl esters of the invention are all known as such. Ethyl 4,6,6-trimethyl-1,3-cyclohexadiene-1-carboxylate has been reported by I. Alkonyi et al. in Acta Chimica Academiae Scientiarium Hungaricae 1957, 12, 289 and is described as chemical intermediate. The methyl analogue has been similarly described by K.-F. Chen et al. in J. Chem. Soc. Perkin Trans. I, 1996, 1213. The methyl or ethyl esters of 4,6,6-trimethyl-3-cyclohexene-1-carboxylic acid have been disclosed as intermediate in J. Org. Chem., 1969, 34, 2196.

However, none of these documents discloses or suggests the organoleptic properties of the compounds of formula (I), or their use in the field of perfumery.

European patent application EP 955290 A1 discloses perfuming ingredients having a general formula that includes the compounds of the present invention. However, in that patent application, the compounds of the present invention are not specifically disclosed, do not belong to preferred class of compounds and there is no mention or suggestion of the particular and unique odor notes that can be conferred by the esters of the present invention.

Now, in perfumery, there is a recognized need for compounds capable of imparting odor notes of the type saffron and spicy so as to complete the needs of perfumers. The use of the compounds of formula (I) fulfils the above-mentioned need.

SUMMARY OF THE INVENTION

The present invention now relates to the use as perfuming ingredient of a lower alkyl ester of 4,6,6-trimethyl-1,3-cyclohexadiene-1-carboxylate or 4,6,6-trimethyl-3-cyclohexene-1-carboxylate as well as the perfuming compositions or perfumed articles associated with this compound.

DETAILED DESCRIPTION OF THE PREFERRED EMBODIMENTS

We have now surprisingly found that a compound of formula (I)

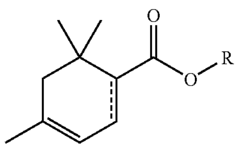

wherein the dotted line represents a single or double bond and R represents a linear or branched $C_1$-$C_4$ alkyl group; can advantageously be used as perfuming ingredient to impart spicy/saffron-like odor notes to the composition in which it is added.

The compounds of formula (I) wherein R is a methyl or ethyl group represent particular embodiments of the invention, and in particular those wherein the dotted line represents a double bond.

Amongst the present compounds, one may cite ethyl 4,6,6-trimethyl-1,3-cyclohexadiene-1-carboxylate which has an odor characterized by a dominant spicy-saffron note and character which is particularly warm and pleasant. The spicy character of this compound has also a slight balsamic-myrrh aspect. Furthermore, the bottom notes of this compound possesses also a cypriol-like nuance.

Another inventive compound is methyl 4,6,6-trimethyl-1,3-cyclohexadiene-1-carboxylate which has an odor similar to that of the ethyl ester mentioned above, but distinguishes itself by a slightly less powerful odor.

Furthermore one may also cite the methyl or ethyl 4,6,6-trimethyl-3-cyclohexene-1-carboxylate. Also these two esters are characterized by a well perceivable saffron note, however the cypriol-like connotation of the above-mentioned ester is here replaced by a rosy-like aspect.

To the contrary of the prior art compounds cited in the above-mentioned EP application, the inventive compounds are characterized by odor properties which lack of, or do not possess significant, floral notes, and all the less character. Furthermore, the odor of the inventive compounds differs also from the one of the prior art ingredients by not imparting a woody character to the composition in which it is added.

These differences lend to the inventive compounds and the prior art compounds to be each suitable for different uses, i.e. to impart different organoleptic impressions.

The ethyl 4,6,6-trimethyl-1,3-cyclohexadiene-1-carboxylate is a particularly preferred embodiment of the invention due to its superior and cleaner saffron note.

As mentioned above, the invention concerns the use of a compound of formula (I) as perfuming ingredients. In other words it concerns a method to confer, enhance, improve or modify the odor properties of a perfuming composition or of a perfumed article, which method comprises adding to such compositions or articles an effective amount of at least a compound of formula (I). By “use of a compound of formula (I)” it has to be understood here also the use of any composition containing compound (I) and which can be advantageously employed in perfumery industry as active ingredients.

These compositions, which are in fact perfuming compositions that can be advantageously employed as perfuming ingredients, also are an embodiment of the invention.

Another embodiment of the present invention is a perfuming composition comprising:

i) as perfuming ingredient, at least one inventive compound as defined above;
ii) at least one ingredient selected from the group consisting of a perfumery carrier and a perfumery base; and
iii) optionally at least one perfumery adjuvant.

By “perfumery carrier” we mean here a material which is practically neutral from a perfumery point of view, i.e. that does not significantly alter the organoleptic properties of perfuming ingredients. The carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials, for example, may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's Verlag-GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

Generally speaking, by "perfumery base" we mean here a composition comprising at least one perfuming co-ingredient. The perfuming co-ingredient is not of the formula (I). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitrites, terpene hydrocarbons, nitrogenous or sulphurous heterocyclic compounds and essential oils, and the perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that the co-ingredients may also be compounds known to release in a controlled manner various types of perfuming compounds.

Generally speaking, by "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that these ingredients are well known to a person skilled in the art.

A composition that includes at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Its is also understood here that, unless otherwise indicated or described, any mixture resulting directly from a chemical synthesis, e.g. without an adequate purification, in which the compound of the invention would be involved as a starting, intermediate or end-product could not be considered as a perfuming composition according to the invention.

Furthermore, the inventive compounds disclosed herein can also be advantageously used in all the fields of modern perfumery to positively impart or modify the odor of a consumer product into which the compound (I) is added. Consequently, a perfumed article comprising:

i) as perfuming ingredient, at least one compound of formula (I) or a composition thereof, and
ii) a consumer product base, is also an embodiment of the present invention.

For the sake of clarity, it has to be mentioned that, by "consumer product base" we mean here a consumer product which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one compound of the invention.

The nature and type of the constituents of the consumer product do not warrant a more detailed description here, which in any case would not be exhaustive, the skilled person being able to select them on the basis of its general knowledge and according to the nature and the desired effect of the product.

Examples of suitable consumer products include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the inventive compounds, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are on the order of 0.01% to 5% by weight, or even more, of the compounds of the invention based on the weight of the composition into which they are incorporated. Concentrations lower than these, such as in the order of 0.01% to 2% by weight, can be used when these compounds are incorporated into perfumed articles.

The inventive compounds can be easily prepared by esterification of the corresponding acids, which are also described in the above-mentioned prior art.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical displacements δ are indicated in ppm with respect to TMS as standard, the coupling constants J are expressed in Hz.

Example 1

Preparation of a Perfuming Composition

A perfuming composition of the "floral-ylang-woody and chypre" type was prepared by admixing the following ingredients:

| Ingredient | Parts by weight |
|---|---|
| Benzyl acetate | 15 |
| Linalyl acetate | 50 |
| Styrallyl acetate | 5 |
| Aldehyde C 11 undecylic | 2 |
| 10%* CETALOX ®[1)] | 1 |
| Citron Sfuma essential oil | 20 |
| Ethylvanilline | 1 |
| Eugenol | 2 |
| EXALTOLIDE ®[2)] | 30 |
| Geranium essential oil | 20 |
| HEDIONE ®[3)] | 50 |
| IRALIA ® Total[4)] | 50 |
| LILYFLORE ®[5)] | 2 |
| Mousse moss | 1 |
| Muscenone Delta[6)] | 2 |
| 1%* Paracresol | 2 |
| Phenethylol | 50 |
| POLYSANTOI ®[7)] | 2 |
| P-Tert-Butylcyclohexyl acetate | 50 |
| Benzyl salicylate | 90 |
| Clary-sage essential oil | 5 |
| VERTOFIX ® Coeur[8)] | 30 |
| Ylang Extra | 20 |
| | 500 |

*in dipropyleneglycol

[1)]Dodecahydro-3a,6,6,9a-tetramethyl-naphtho[2,1-b]furan; origin: Firmenich SA, Geneva, Switzerland

[2)]Pentadecenolide; origin: Firmenich SA, Geneva, Switzerland

[3)]Methyl dihydrojasmonate; origin: Firmenich SA, Geneva, Switzerland

[4)]Mixture of isomers of methylionones; origin: Firmenich SA, Geneva, Switzerland

[5)]2,5-Dimethyl-2-indanmethanol; origin: Firmenich SA, Geneva, Switzerland

[6)]3-Methyl-4/5-cyclopentadecen-1-one; origin: Firmenich SA, Geneva, Switzerland

[7)]3,3-Dimethyl-5-(2,2,3-trimethyl-3-cyclopenten-1-yl)-4-penten-2-ol; origin: Firmenich SA, Geneva, Switzerland

[8)]Methyl cedryl ketone; origin International Flavors & Fragrances, USA

The addition of 5 parts by weight of ethyl 4,6,6-trimethyl-1,3-cyclohexadiene-1-carboxylate to the above-described perfuming composition imparted to the fragrance of the latter an harmonious spicy note of the natural saffron type, which transformed the chypre aspect in a positive manner, providing thus a richer and more natural fragrance.

This effect could not be obtained by the addition of any of the compounds cited in EP 955290.

Furthermore, the addition of the same amount of Safranal to the above-described perfuming composition, in view of obtaining the same saffron note, resulted in a polarized fragrance having a medicinal aspect.

What is claimed is:

1. A method to provide or impart a saffron odor note to a perfuming composition or of a perfumed article, which method comprises adding to the composition or article an effective amount of at least a compound of formula (I)

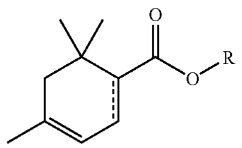

wherein the dotted line represents a double bond and R represents a methyl or ethyl group, to thus provide or impart the saffron note to the composition or article.

2. The method of claim 1, wherein the compound is added to a composition comprising at least one ingredient selected from the group consisting of a perfumery carrier and a perfumery base; and optionally, at least one perfumery adjuvant to form a perfuming composition having a saffron note.

3. The method of claim 1, wherein the compound is added to an article that includes a consumer product base to prepare a perfumed article having a saffron note.

4. The method of claim 3, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

5. The method of claim 2, wherein the perfuming composition is added to an article that includes a consumer product base to prepare a perfumed article having a saffron note.

6. The method of claim 5, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

7. The method of claim 1, wherein the compound is methyl 4,6,6-trimethyl-1,3-cyclohexadiene-1-carboxylate.

* * * * *